United States Patent [19]

White

[11] Patent Number: 4,558,136

[45] Date of Patent: Dec. 10, 1985

[54] PREPARATION OF 2-BENZOXAZOLINONES

[75] Inventor: Alan W. White, Kingsport, Tenn.

[73] Assignee: Eastman Kodak Company, Rochester, N.Y.

[21] Appl. No.: 746,949

[22] Filed: Jun. 21, 1985

Related U.S. Application Data

[63] Continuation of Ser. No. 487,930, Apr. 22, 1983, abandoned.

[51] Int. Cl.[4] .......................................... C07D 263/56
[52] U.S. Cl. .................................................. 548/221
[58] Field of Search ........................................ 548/221

[56] References Cited

U.S. PATENT DOCUMENTS 3,657,265  4/1972  Kober et al. ..................... 548/219
4,454,322  6/1984  Kervennal et al. ................ 548/221

Primary Examiner—Marion C. McCamish
Assistant Examiner—S. A. Gibson
Attorney, Agent, or Firm—Clyde L. Tootle; J. Frederick Thomsen; Daniel B. Reece, III

[57] ABSTRACT

Disclosed is a process for preparing 2-benzoxazolinones by reacting a 2-nitrophenol compound with carbon monoxide in the presence of a palladium catalyst and a tertiary amine.

9 Claims, No Drawings

PREPARATION OF 2-BENZOXAZOLINONES

This is a continuation of application Ser. No. 487,930 filed Apr. 22, 1983 now abandoned.

This invention pertains to a novel process for the preparation of 2-benzoxazolinones and, more particularly, to the preparation of 2-benzoxazolinones by the reductive carbonylation of 2-nitrophenols.

The known methods for preparing unsubstituted and substituted 2-benzoxazolinones include reacting 2-aminophenols with urea (C.A. 56:15516g), treating N-(2-hydroxyphenyl)carbamic acid esters with a strong base (C.A. 62:11796g), treating salicylhydroxamic acid with benzenesulfonyl chloride (C.A. 69:27377b) and by treating a halogenated salicylhydroxamic acid with ethyl chloroformate. The preparation of urethanes such as diethyl toluene-2,4-dicarbamate by reacting a hydroxyl group-containing organic compound, an organic nitro-compound and carbon monoxide under elevated temperature and pressure in the presence of a catalyst consisting of a mixture of a tertiary organic amine and a platinum group metal or compound is disclosed in U.S. Pat. No. 3,993,685.

I have discovered that 2-benzoxazolinones can be prepared by reacting a 2-nitrophenol compound with carbon monoxide at elevated temperature and pressure in the presence of a catalytic amount of a palladium catalyst and an organic tertiary amine. The 2-benzoxazolinone compounds are useful as antibacterial and antifungal agents (C.A. 64:19586f), as hypnotics and sedatives (C.A. 56:15516g) or as intermediates in the manufacture of other useful chemicals (C.A. 75:50401a, 50404d).

The process may be carried out over a wide range of temperature and pressure, e.g. from about 50° to 250° C. and about 100 to 2500 psig. Normally, satisfactory results may be achieved by using a temperature in the range of about 110° to 180° C. and a pressure of about 400 to 1200 psig. The process typically is performed by charging an inert solvent and the nitrophenol compound to a pressure vessel such as an autoclave, pressurizing the vessel with carbon monoxide and then heating the vessel to the desired reaction temperature. Hydrocarbons such as hexene, heptane, benzene, toluene and xylene are examples of the inert solvents which can be used. Alternatively, certain of the tertiary amines, such as pyridine, useful in the process may also function as the inert solvent.

The palladium catalysts suitable for use in the process may be palladium metal or a palladium compound, particularly palladium salts such as palladium chloride and palladium acetate. The amount of palladium (as Pd) that will be catalytically effective can be varied considerably, for example from about 0.05 to 10.0 weight percent based on the weight of the 2-nitrophenol compound. Normally, the amount of palladium catalyst is in the range of about 0.5 to 2.0 weight percent (same basis).

The tertiary amine required in the practice of my novel process is, in general, not critical and may be selected from a wide variety of acyclic, cyclic and aromatic amines. Representative examples of such amines are described in U.S. Pat. No. 3,993,685. Pyridine is the preferred tertiary amine. The amine:2-nitrophenol mole ratio should be at least about 1 and may be as high as 50 when an otherwise suitable tertiary amine is employed as the reaction solvent.

The 2-nitrophenol reactant may be unsubstituted or substituted with a wide variety of substituents which do not affect formation of the desired 2-benzoxazolinone. Examples of such substituents are alkyl, alkoxy, aryl, aryloxy, chlorine, alkanoylamino, aroylamino, alkoxycarbonylamino, alkylsulfonamido, arylsulfonamido, sulfamoyl, carbamoyl, cyano, carboxyl, etc.

The process of my invention is further illustrated by the following examples.

EXAMPLES 1–6

2-Nitrophenol (3.5 g) was reacted in a glass-lined autoclave with carbon monoxide in the presence of varying amounts of palladium chloride, toluene, and pyridine using varying temperatures, pressures and reaction times. After charging the 2-nitrophenol, palladium chloride, toluene and pyridine the autoclave was sealed, pressurized with carbon monoxide to the desired pressure, heated to the desired reaction temperature and maintained at the reaction temperature for a predetermined period of time (reaction time). Upon completion of the reaction time the autoclave was cooled, vented and the crude product was analyzed by gas chromatography using octadecane as an internal standard. In Example 3 the crude product was isolated by filtration and purified by dissolving it in aqueous ethanol, treating the solution with charcoal and recrystallizing after filtering off the charcoal. The purified product was confirmed to be 2-benzoxazolinone by infrared, nuclear magnetic resonance and mass spectroscopy.

Table I shows the amounts of palladium chloride (g), toluene (ml), and pyridine (ml) and the temperature (°C.), pressure (psig, at room temperature) and reaction time (hrs.) employed in each of six runs. The yields (percent of theory) given are based on gas chromatography analysis.

TABLE I

| Ex. | PdCl$_2$ | Pyridine/Toluene | Temp. | Pressure | Reaction Time | Yield |
|---|---|---|---|---|---|---|
| 1 | 0.220 | 5/5 | 160 | 1000 | 5 | >80 |
| 2 | 0.044 | 2/8 | 150 | 700 | 3 | ~60 |
| 3 | 0.220 | 5/5 | 120 | 1000 | 5 | 75 |
| 4 | 0.220 | 5/5 | 160 | 500 | 5 | 91 |
| 5 | 0.220 | 2/8 | 160 | 1000 | 5 | 86 |
| 6 | 0.088 | 2/8 | 160 | 700 | 8 | 82 |

The invention has been described in detail with particular reference to preferred embodiments thereof, but it will be understood that variations and modifications can be effected within the spirit and scope of the invention.

I claim:

1. Process for the preparation of 2-benzoxazolinones by reacting a 2-nitrophenol compound with carbon monoxide at elevated temperature and pressure in the presence of a catalytic amount of an unsupported palladium catalyst selected from the group consisting of palladium chloride and palladium acetate and at least one mole of a tertiary amine per mole of 2-nitrophenol compound.

2. A process according to claim 1 wherein said elevated temperature is 50° C. to 250° C.

3. A process according to claim 2 wherein said elevated pressure is 100 to 2500 psig.

4. A process according to claim 3 wherein said catalytic amount of palladium catalyst is 0.5 to 10.0 weight percent based on weight of 2-nitrophenol.

5. A process according to claim 4 wherein the mole ratio of tertiary amine to 2-nitrophenol is 1:1 to 50:1.

6. A process according to claim 5 wherein said tertiary amine is pyridine.

7. A process according to claim 6 wherein said elevated temperature is 110° C. to 180° C.

8. A process according to claim 7 wherein said elevated pressure is 400 to 1200 psig.

9. A process according to claim 8 wherein said catalytic amount of palladium catalyst is 0.5 to 2.0 weight percent based on weight of 2-nitrophenol.

* * * * *